(12) United States Patent
Yiu

(10) Patent No.: US 6,780,381 B2
(45) Date of Patent: Aug. 24, 2004

(54) PIPETTOR AND EXTERNALLY SEALED PIPETTE TIP

(76) Inventor: Felix H. Yiu, 825 S. Primrose Ave. Ste I, Monrovia, CA (US) 91016

( * ) Notice: Subject to any disclaimer, the term of this patent is extended or adjusted under 35 U.S.C. 154(b) by 74 days.

(21) Appl. No.: 10/119,100

(22) Filed: Apr. 8, 2002

(65) Prior Publication Data

US 2003/0190263 A1 Oct. 9, 2003

(51) Int. Cl.⁷ .................................................. B01L 3/02
(52) U.S. Cl. ...................... 422/100; 422/99; 73/864.01; 73/864.14
(58) Field of Search ................ 422/100, 99; 73/864.01, 73/864.11, 864.14

(56) References Cited

U.S. PATENT DOCUMENTS

| | | | |
|---|---|---|---|
| 3,732,734 A | 5/1973 | Avakian ................... 73/425.6 |
| 4,072,330 A | 2/1978 | Brysch ...................... 285/239 |
| 4,418,580 A | 12/1983 | Satchell et al. .......... 73/864.13 |
| 4,478,094 A | 10/1984 | Salomaa et al. ......... 73/863.32 |
| 4,589,421 A | 5/1986 | Ullman ....................... 128/763 |
| 4,748,859 A | 6/1988 | Magnussen, Jr. et al. 73/864.01 |
| 4,824,641 A | 4/1989 | Williams ................... 422/100 |
| 5,200,151 A | 4/1993 | Long ........................... 422/100 |
| 5,209,128 A | 5/1993 | Whelan ................... 73/864.03 |
| 5,218,875 A | 6/1993 | Volpe et al. ............. 73/864.01 |
| 5,232,669 A * | 8/1993 | Pardinas .................... 422/100 |
| 5,496,523 A | 3/1996 | Gazit et al. ................ 422/100 |
| 5,497,670 A | 3/1996 | Carl ......................... 73/863.32 |
| 5,604,101 A | 2/1997 | Hanley et al. ................. 435/6 |
| 5,660,792 A | 8/1997 | Koike .......................... 422/63 |
| 5,736,105 A | 4/1998 | Astle .......................... 422/100 |
| 5,827,745 A | 10/1998 | Astle ........................... 436/54 |
| 6,116,099 A | 9/2000 | Carl ........................ 73/864.14 |
| 6,132,582 A | 10/2000 | King et al. ................. 204/604 |
| 6,168,761 B1 | 1/2001 | Kelly et al. ................ 422/100 |
| 6,171,553 B1 | 1/2001 | Petrek ........................ 422/100 |
| 6,182,719 B1 | 2/2001 | Yahiro ........................ 141/130 |
| 6,197,259 B1 | 3/2001 | Kelly et al. ................ 422/100 |
| 6,258,324 B1 | 7/2001 | Yiu ............................. 422/100 |
| 6,415,669 B1 | 7/2002 | Carl ........................ 73/864.14 |

OTHER PUBLICATIONS

Webster's Ninth new Collegiate Dictionary, Merriam–Webster, Inc, (1987) p. 469.*

* cited by examiner

Primary Examiner—Jan M. Ludlow
(74) Attorney, Agent, or Firm—Cislo & Thomas LLP

(57) ABSTRACT

A pipettor uses no pistons in order to provide highly automated, precise and accurate pipetting operations. Additionally, a self-aligning pipette tip enables better engagement of such pipette tips by the pipettor. The pipette tips may be automatically engaged and locked into place by the pipettor and may be automatically disengaged to enable highly-automated pipetting processes for industrial and laboratory purposes. Open proximal ends of the pipette tips are engaged by a pipette block, which then forms a temporary seal with the individual pipette tips. Displacement of the pipette block with respect to the pipette tips increased or decreases the effective volume of the pipette tip allowing it to aspirate or expel fluids in a precise, accurate, and predictable way.

29 Claims, 14 Drawing Sheets

PIPETTOR AND EXTERNALLY SEALED PIPETTE TIP

BACKGROUND OF THE INVENTION

1. Field of the Invention

This invention relates to pipettors and pipette tips and more particularly to a piston free pipettor and a self-aligning and self-sealing pipette tip.

2. Description of the Related Art

Pipetting systems are used in laboratories for the transfer of relatively small quantities of liquids in a precise and accurate manner. The liquid is normally drawn into the tips by suction and is subsequently released into the wells of microtiter plates or other receptacles. Frequently the transfer involves samples, which are moved from one set of spaced receptacles to another set of receptacles.

The use of pipette devices for the transfer and dispensing of precise quantities of fluids in analytical systems is well known as is the use of disposable tip members for such pipettes. Disposable tips accommodate the serial use of such pipette devices in the transfer of different fluids without carryover or contamination of a second sample from a disposable pipette tip used with a first sample. The first tip is discarded and replaced by a second disposable tip before pipetting the second sample.

Generally speaking, prior disposable pipette tips are formed of a plastic material and are of a hollow, elongated, generally conical shape with an open proximal end for receiving and releasably mating with the distal end of an elongated, generally conical, pipette tip mounting shaft of a pipette device. Ideally, the disposable tip should slide easily onto the mounting shaft to an axial position adjacent a lower end of a tip ejection mechanism of the pipette device. Thus located, the pipette tip should be laterally stable on the shaft, free from external rocking relative to the shaft (as during "touching off"), and should form a fluid tight annular seal with the mounting shaft. Then when it is desired to replace the tip with a new tip, the pipette tip should be easily removed from the mounting shaft by operation of a tip ejection mechanism.

To meet the desired sealing criteria for disposable pipette tips on pipette tip mounting shafts, the inner surface and side walls of the proximal portions of most pipette tips may be axially tapered at a one to one and a half degree greater angle than the distal end of the pipette tip mounting shaft and form an axially elongated frusto-conical annular sealing band. The sealing band may be dimensioned to stretch outwardly ("hoop stretch") as the distal end of the elongated generally conical pipette tip mounting shaft is forced into the proximal end of the tip to fly seat the tip on the shaft and to create an axially elongated annular fluid tight seal between the sealing band and the mounting shaft. Other pipette tips, may include a plurality of axially-spaced compressible annular sealing rings on an inner surface of the proximal end portion of such tips. The rings create multiple axially spaced fluid tight annular seals between the outer surface of the pipette tip mounting shaft and the inner surface of the proximal end portion of the tip which by virtue of the axially spaced rings is laterally stabilized against undesired rocking on the shaft during touching off.

The design criteria for disposable pipette tips demand that they be stably mountable on and form a fluid tight seal with a pipette mounting shaft is more easily achieved than the design criteria that disposable pipette tips slide easily onto a pipette tip mounting shaft to an axial location forming a fluid tight seal and then be easily removable from the mounting shaft when it is desired to replace the tip.

As previously stated, standard small and moderate volume pipette tips include a frusto-conical annular sealing band or inner surface for engaging and sealing with the tapered distal end of a pipette tip mounting shaft. The angle of taper of the sealing surface usually approximates (e.g., one and one-half degrees greater than) that of the mounting shaft (e.g., two to five degrees). Thinning the side wall of the standard small and moderate volume pipette tips in the region of such a sealing band does little to reduce the mounting and ejection forces required to move such a tip to a sealing location and then eject the pipette tip from the mounting shaft. In forming the desired annular seal, the frusto-conical annular region is required to stretch like a hoop (hoop stretch) outwardly normal to the mating sloping surface of the pipette tip mounting shaft. Large reactive forces in the tip material resist such hoop stretching and require the exertion of large axial forces (e.g., one to three (1–3) or more pounds) on the tip in order to mount the tip on the mounting shaft and create the necessary annular fluid tight seal. Such reactive forces increase as the tip is driven toward the tip ejection mechanism of the associated pipette device.

Due to the foregoing, it can be seen that the efficient mounting of disposable pipette tips by the insertion of a mounting shaft into the pipette tip entails some problems that have yet to be resolved by the art which the present invention addresses.

Disposable pipette tips are commonly mounted and stored in sterilizable racks. Such racks commonly include a support tray having an array of holes for receiving distal ends of pipette tips to vertically orient the pipette tips in a spaced rectilinear pattern with open proximal ends of the tips exposed to receive the mounting shafts of a pipette device onto which the pipette tips are to be mounted. For example, to mount the disposable pipette tips contained in a tip rack on the shafts of a multi-channel pipette, the pipette device is placed over the rack with its several mounting shafts aligned with the open proximal ends of an aligned series of the pipette tips. After a slight initial insertion of the mounting shafts into the open proximal ends of the aligned pipette tips, a relatively large downward force is exerted on the pipette device to drive the mounting shafts into the tip members. The pipette tips are thus very firmly seated on the mounting shafts and are lifted from the rack with upward movement of the multi-channel pipette.

Unfortunately, in practice, such multiple pipette tip mounting procedures often result in some of the pipette tips being mounted at different axial orientations on some of the mounting shafts or mandrels. However, if the pipettor channels are ganged together, the axial orientation would be the same on all tips. However, the force of the seal may vary on each tip due to the variance in internal tip sizes at the places of sealing. In an attempt to eliminate such non-uniform mounting of pipette tips on the several channels of a multi-channel pipette, users often rock the pipette as the mounting shafts are driven by relatively high axial forces into the tips supported by a pipette tip rack to drive the tips toward the lower surface of the tip ejector mechanism of the pipette.

Additionally, the prior pipette tips frequently relied upon the use of O-rings to provide a seal between the pipette tip and the mandrel or manifold into which the pipette tip fit. Several disadvantages arise from the use of O-rings, not the least of which is the greater expense and manufacturing. Additionally, O-rings require lubrication and other activities leading to high maintenance with respect to such O-rings. O-rings need replacement from time to time and due to compression introduce an element of unreliability into the volumes pipetted especially as needed amounts of pipetted liquids become smaller and smaller and progress further and further into the microvolume range.

Consequently, it would be an advance in the art to provide pipette tips that generally do not require a relatively high degree of force or pressure in order to secure them to a mounting shaft or other mounting construction. It would additionally be advantageous to provide such a system to allow a single precise and accurate machine to both aspirate and dispense liquids, as well as to hold the pipette tips in place. This would allow more automated processing of pipetting procedures and allow human attention to be devoted to other more important activities. The present invention provides solutions to these and other problems and disadvantages in the prior art.

SUMMARY OF THE INVENTION

The present invention provides an automated pipetting machine that automatically sets and dislodges the pipette tips, as well as providing automatic pipetting operations.

Instead of the usual configuration where a piston moves relative to the pipette tip, a pipette block engages and surrounds the open proximal end of the pipette tips. The pipette tips themselves are held in place with respect to a chassis by a locking plate system. The pipette block then moves vertically with respect to the locking plate system in order to apply or diminish pressure within the pipette tip. This respectively causes the pipette tip to expel/dispense or aspirate fluid at the tip of the pipette. A sliding seal is present between the open proximal end of the pipette tip and the circumscribing surface of the pipette block. By means of a precision motor, precise and accurate amounts of fluid can be dispensed or aspirated by the pipette tips.

Additional motors allow for the automatic locking and unlocking of the locking plate system so that the pipette tips are automatically locked and unlocked into place. Additionally, a third motor disposes the entire pipetting assembly vertically with respect to underlying microtiter plates, other receptacles, and/or pipette tip holders.

The pipettor and pipette tips of the present invention enable precise and accurate amounts of fluid to be pipetted in a piston-less system that is reliable and which lends itself to a high degree of automation.

The present invention also provides pipette tips that require no O-rings in order to provide a reliable seal. For this and other reasons, manufacturing costs are lowered and a more advantageous pipette tip is provided that is reliable and useful in nature.

OBJECTS OF THE INVENTION

It is an object of the present invention to provide an automatic pipettor.

It is yet another object of the present invention to provide a pipette tip that may be used in the pipettor of the present invention without conventional O-rings, as well as other pipetting systems whether manual or automated.

It is yet another object of the present invention to provide a relatively low maintenance, multiple-pipette tip pipettor that is free of pistons while delivering precise and accurate amounts of fluids by pipetting.

It is yet another object of the present invention to provide a pipettor that lends itself to automated processes.

It is yet another object of the present invention to provide a disposable pipette tip.

It is yet another object of the present invention to provide a pipette tip that is inexpensive to manufacture.

It is yet another object of the present invention to provide a pipette tip that is usefully implemented in both manual and automated processes.

It is yet another object of the present invention to provide a pipette tip that can be used in plungerless and pistonless pipettors.

It is yet another object of the present invention to provide a pipette tip that provides a seal with the adjacent pipetting mandrel or manifold without the use of O-ring seals.

These and other objects and advantages of the present invention will be apparent from a review of the following specification and accompanying drawings.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
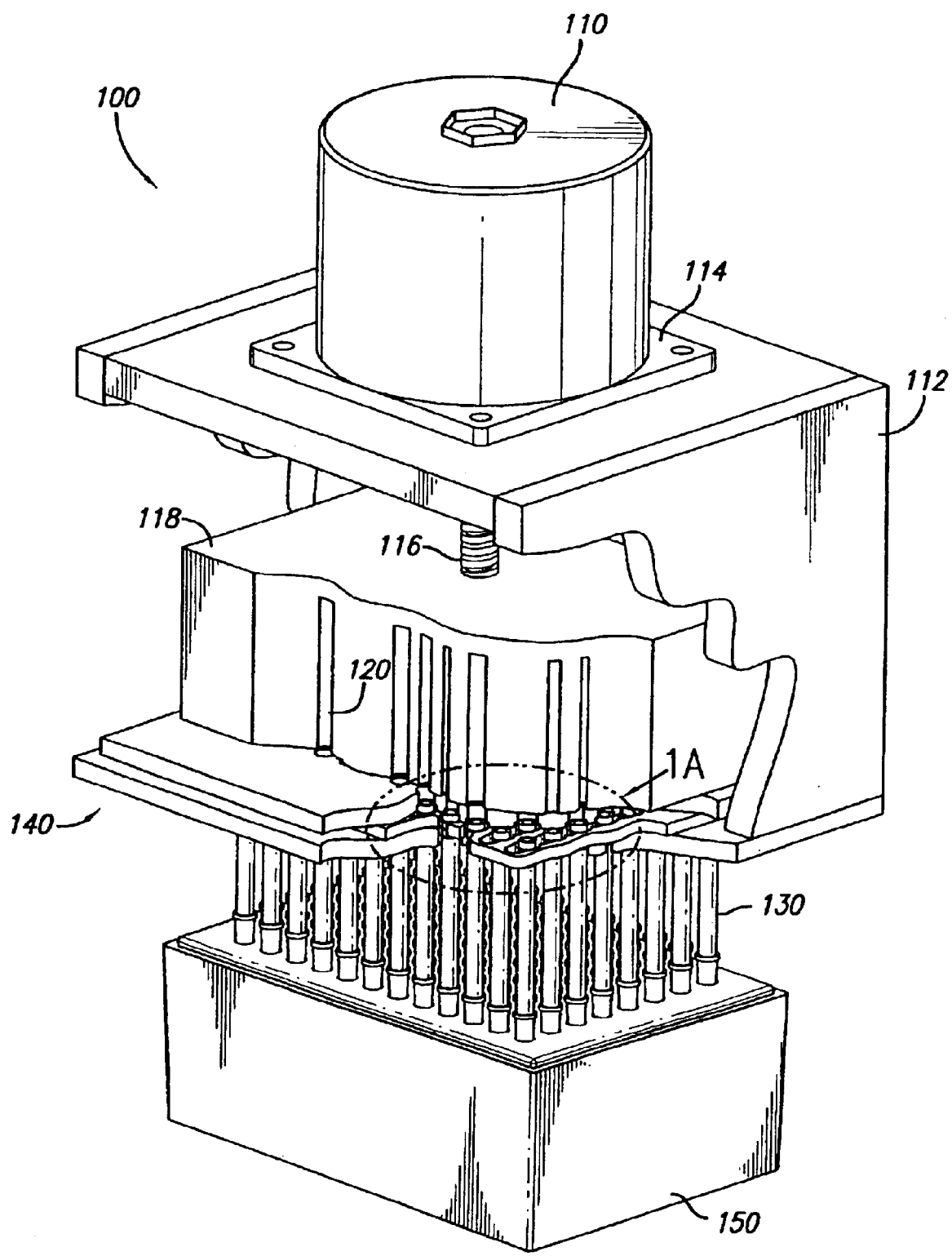
FIG. 1 is a left side perspective and partial cutaway view of the pipettor of the present invention, with a holder of disposable pipette tips having the open proximal pipette tip ends passing through the locking plate and bottom stationary plate.

The automatic and motorized pipettor 100 is shown in FIG. 1 in a perspective and partial cutaway view indicating a variety of the different features of the present invention. A precision motor 110 (that may operate in a stepwise manner) is attached to the chassis 112 by a motor mount 114. The motor 110 may be controlled by a computer or other automated processing device (not shown). A large threaded screw 116 passes through the motor 110 and the motor mount 114. The lower end of the threaded screw 116 is attached to the pipette block 118 into which a plurality of precision holes are bored. The holes 120 engage the pipette tips 130 so as to cause there to be a sealing yet slidable relationship between the pipette tips 130 and the smooth interior of the pipette lock holes 120.

The pipettes 130 are held in place relative to the chassis 112 by a locking plate assembly 140. The locking plate assembly 140 allows the pipette tips 130 to pass through the locking plate assembly until the pipette tips 130 are fully engaged by the pipette block 118. The pipette tips 130 are then locked into place by the locking plate assembly. The pipette block 118 may then raise and lower relative to the locking plate assembly 140 in order to aspirate or expel fluid from the open distal end of the pipette tips 130.

Figure 1A:
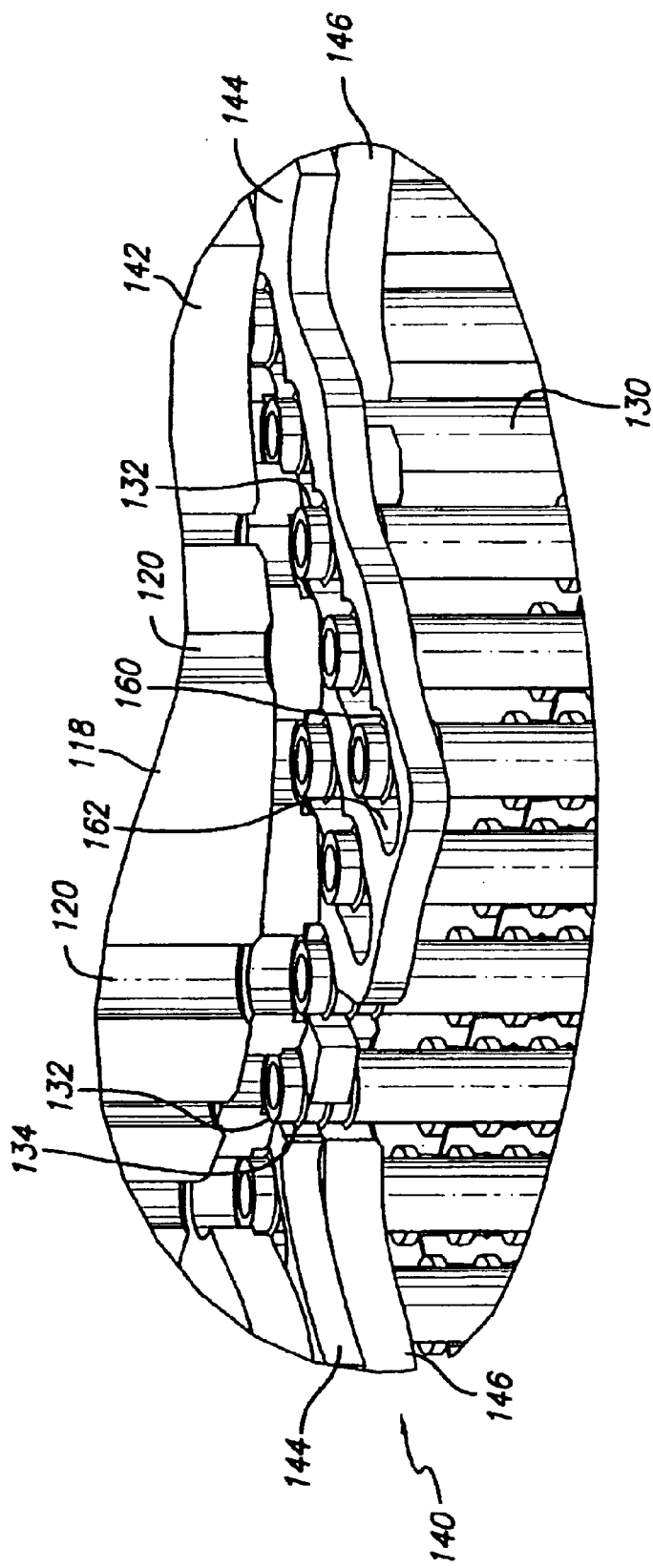
FIG. 1A is a close up of the open proximal pipette tip ends passing through the locking plate structure as indicated by circle 1A in FIG. 1.

FIG. 1A shows in greater detail the pipette tips 130 and their open proximal end 132 passing through the locking plate assembly 140. As shown in FIG. 1A, the locking plate assembly 140 has an upper stationary plate 142 in middle and sliding locking plate 144 and a lower or bottom stationery plate 146.

As can be seen in FIG. 1A, the open proximal ends 132 of the pipette tips 130 have adjacent to them a set of three circumscribing ribs 134. The circumscribing ribs 134 act in concert as a sealing system with the circumscribing ribs 134 as sealing members. The circumscribing ribs 134 engage the smooth interiors of the pipette block bores 120 in order to provide a seal between the ambient environment and the confines of the bore 120. However, in some instances a single rib 134 will suffice.

Shown in FIG. 1A, the locking plate assembly 140 initially allows the proximal ends 132 of the pipette tips 130 to pass through the pipette apertures defined by the locking plate assembly. This is also shown in FIGS. 2 and 3.

Figure 2:
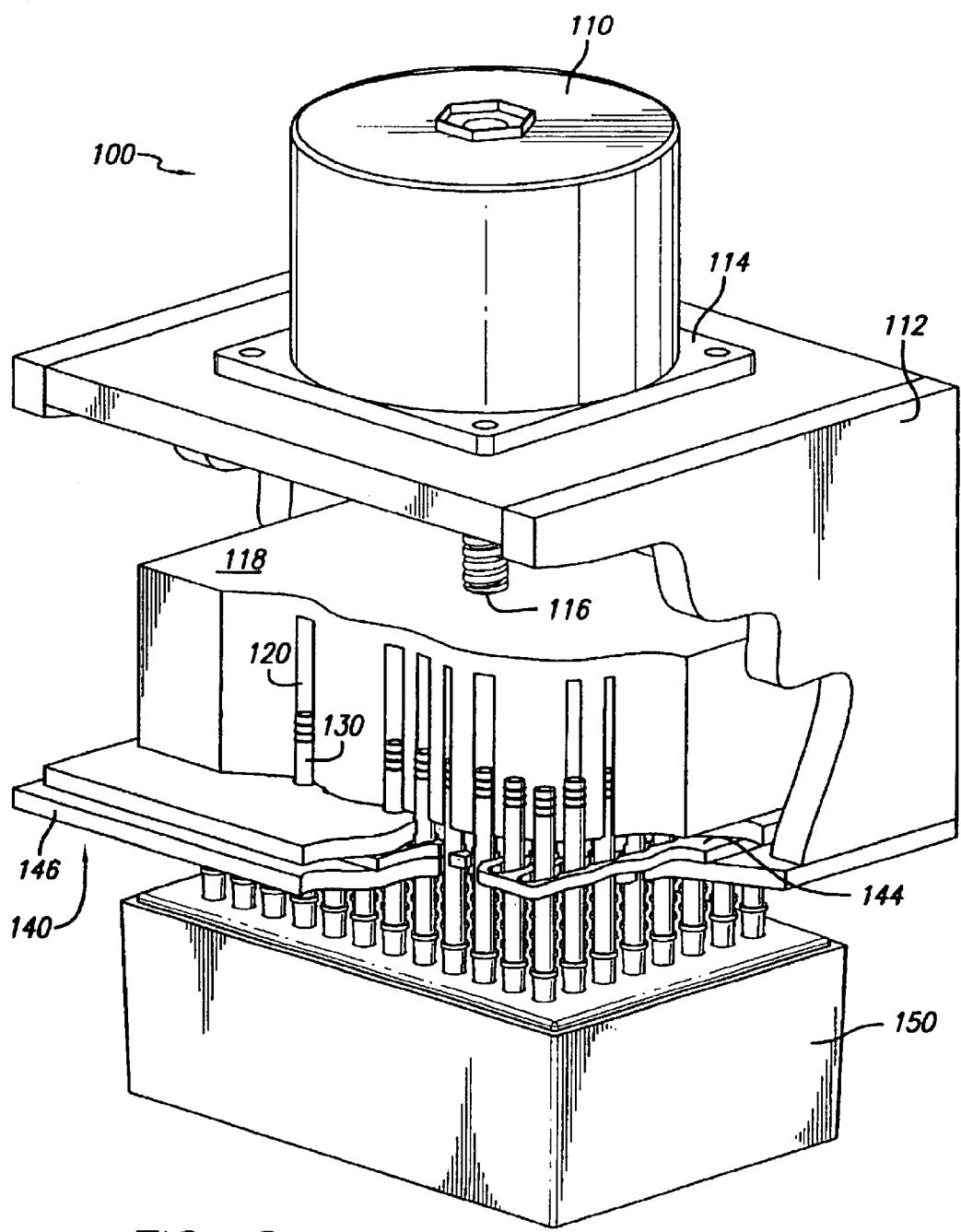
FIG. 2 is a left side perspective and partial cutaway view of the pipettor as the pipette block engages the open proximal pipette ends as such ends pass through the locking plate assembly.

In FIG. 2, the chassis 112 continues to descend towards the pipette holder 150, and the pipettes 130 travel increasingly farther into the bores 120 present in the pipette block 118. The pipette tips 130 travel freely through the locking plate assembly 140 as the middle locking plate 144 is in the open and unlocked position.

Figure 3:
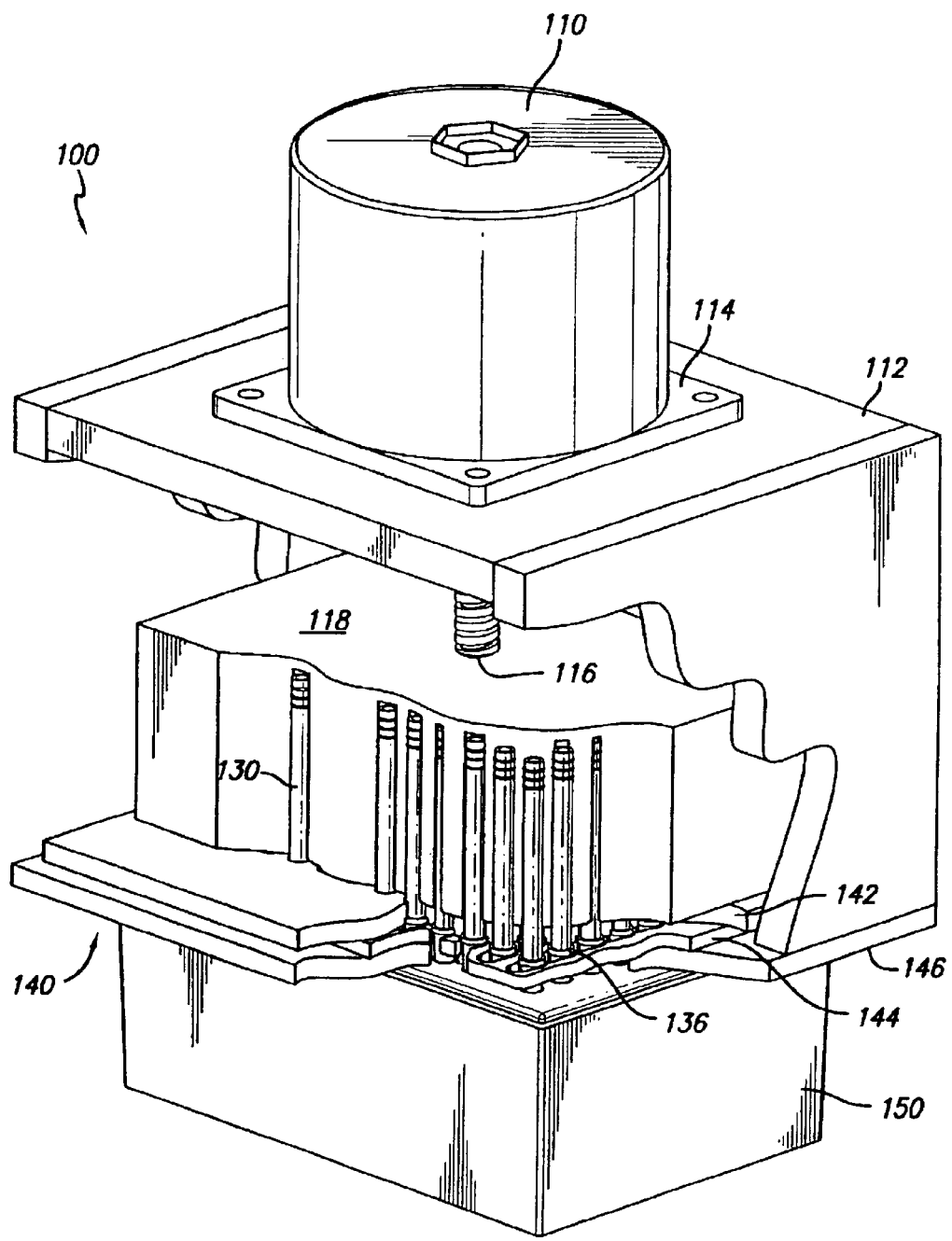
FIG. 3 is a left side perspective and partial cutaway view of the pipettor as the locking plate reaches the locking rings of the pipettes.

In FIG. 3, the chassis 112 has descended down to a position generally proximate the pipette holder 150. Note should be taken that the motor 110 has generally not been involved in this process. The pipette engagement process is generally controlled by a separate vertical displacement motor for the chassis (FIG. 6) about which more is described later. Additionally, the threaded screw 116 generally does not turn during this process, as there is no relative displacement occurring between the pipette block 118 and the locking plate assembly 140 during the pipette-engagement process.

As shown in FIG. 3, the locking plate assembly 140 has descended so that the locking flanges 136 of the pipette tips 130 are positioned above the locking plate 144 but beneath the upper plate 142. The locking flanges 136 may be held above the pipette holder 150 by the pipettes 130 themselves, as the height of the pipette holder 150 may be less than the height of the locking flanges 136. Consequently, the locking flanges 136 stand above the pipette holder although the pipette holder reliable and predictably holds the pipette tips 130 in an upright position.

Figure 4:
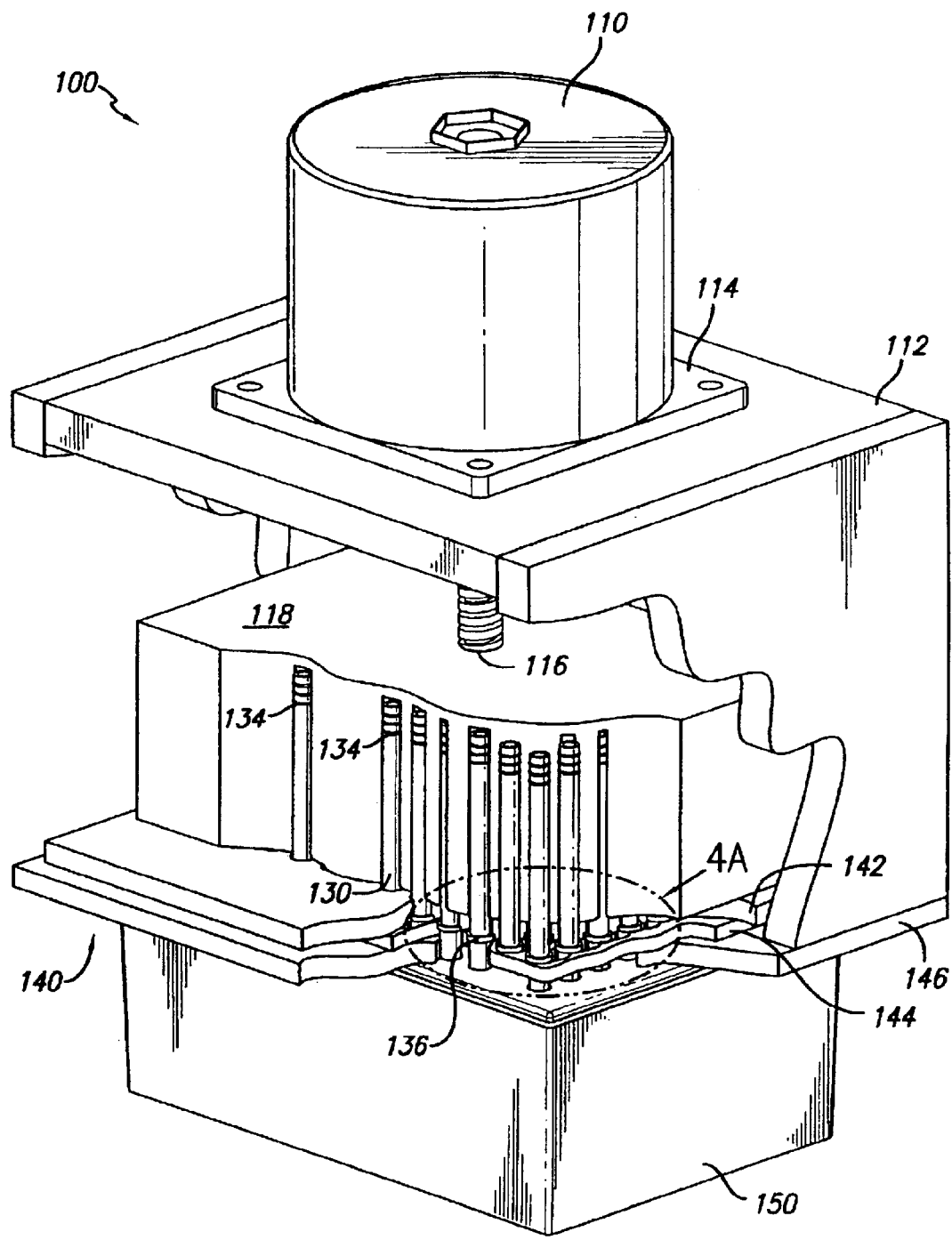
FIG. 4 is a left side and partial cutaway view of the pipettor of the present invention showing the locking of the pipettes by the locking plate assembly.

In FIG. 4, the locking plate 144 travels laterally relative to the pipette tips 130, so as to lock the locking flanges 136 between the locking plate 144 and the upper stationery plate 142. This locking relationship is shown in enlarged form in FIG. 4A, where the interior perimeter of the locking plate 144 is wide enough on one side 160 to allow the locking flange 136 to pass through but is only wide enough for the pipette body at a second end 162.

Figure 4A:
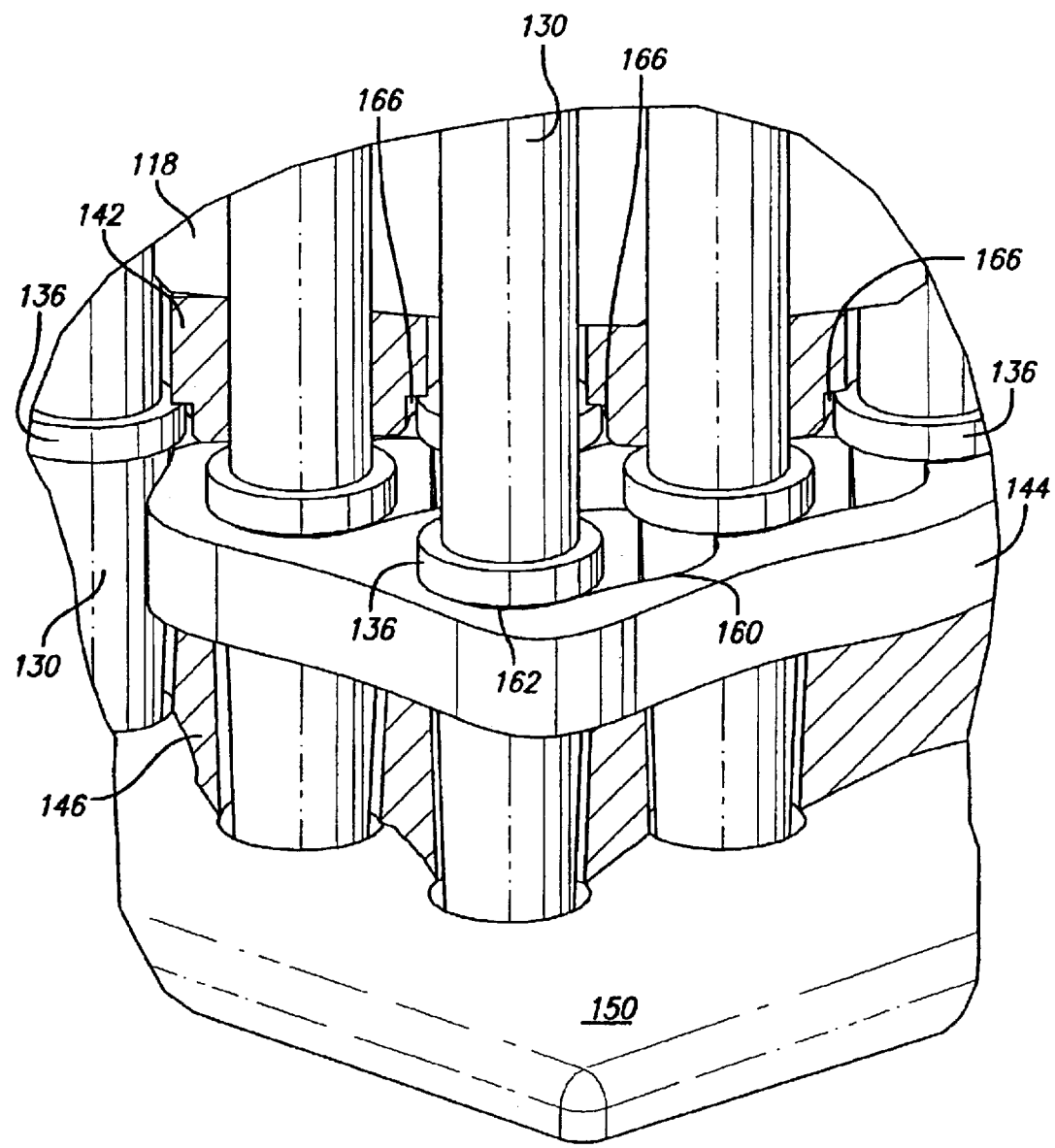
FIG. 4A is an enlarged view of circle 4A of FIG. 4 showing the locking plate locking the pipettes into place.

When the locking plate 144 moves relative to the pipette 130, it either locks or unlocks the locking flange 136 in place with respect to the locking plate assembly 140. As shown in FIG. 4A, the locking flanges are locked in place as the upper plate 142 has flange receiving notches 166, which prevent the upper plate 142 from traveling downwardly past the locking flanges 136 and correspondingly prevents the locking flanges 136 from traveling upwardly past the upper plate 142. When the middle locking plate 144 locks the locking flange 136 in place, the locking flange 136 is trapped vertically with respect to both the upper plate 142 and the middle plate 144. The lower plate serves as a protective and spacing mechanism for the middle plate 144 and provides more secure operation for the locking process. The horizontal movement of the pipette 130 is restrained by its inserted disposition into the smooth and close fitting bore 120 in the pipette lock 118.

Figure 4B:
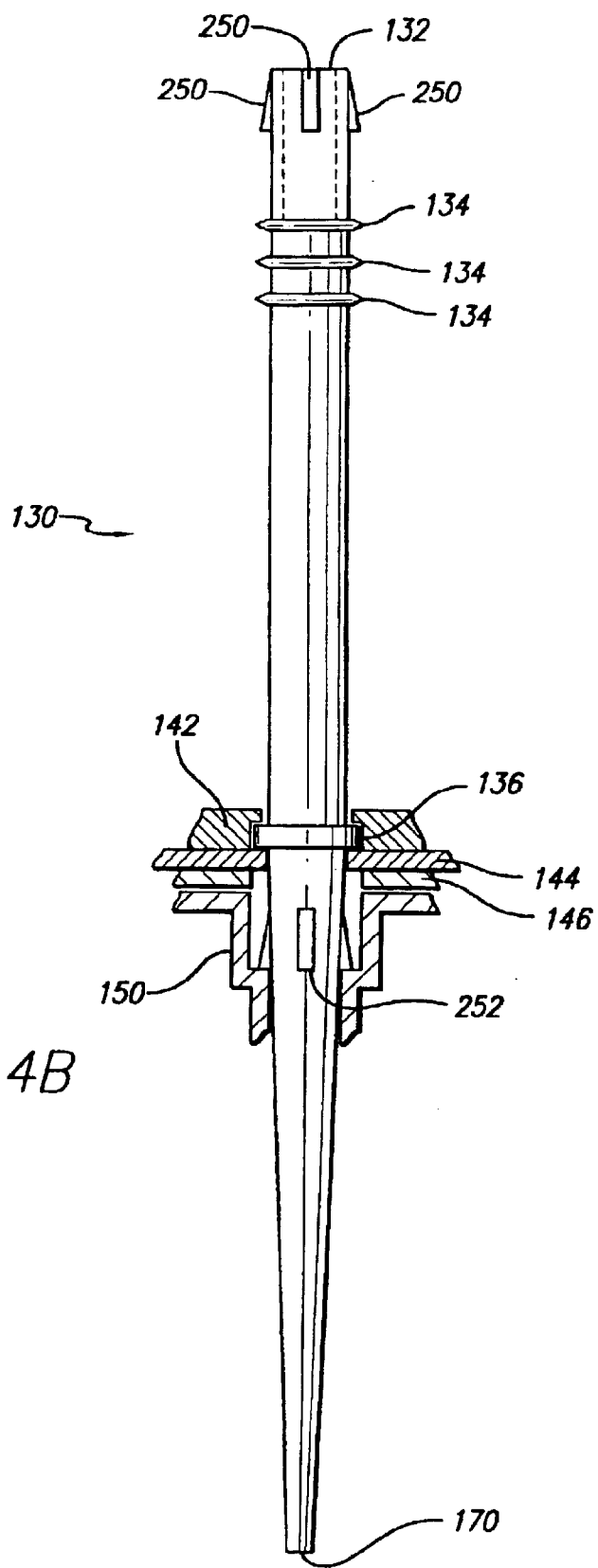
FIG. 4B is a side and partial cross sectional view of a pipette tip held in a holder as shown in FIGS. 4 and 4A indicating additional aligning supports used to support the pipette tip in the pipette tip holder and the locking plate adjacent the locking flange.

As seen in FIG. 4B, the pipette tip 130 may be held upright in the pipette holder 150 with assistance by the pipette holder alignment taps 252. The holder alignment taps 252 serve to hold the pipette tip 130 a small distance above the pipette holder 150. The holder alignment taps 252 serve to engage the pipette holder 150 instead of the locking flange 136 or the distal end 170 of the pipette tip 130. This allows the locking flange 136 to stand away from the upper surface of the pipette holder 150 without forcing the distal end 170 of the pipette tip 130 contacting the pipette holder 150. Alternatively, the alignment taps 252 may be omitted if circumstances warrant.

Figure 5:
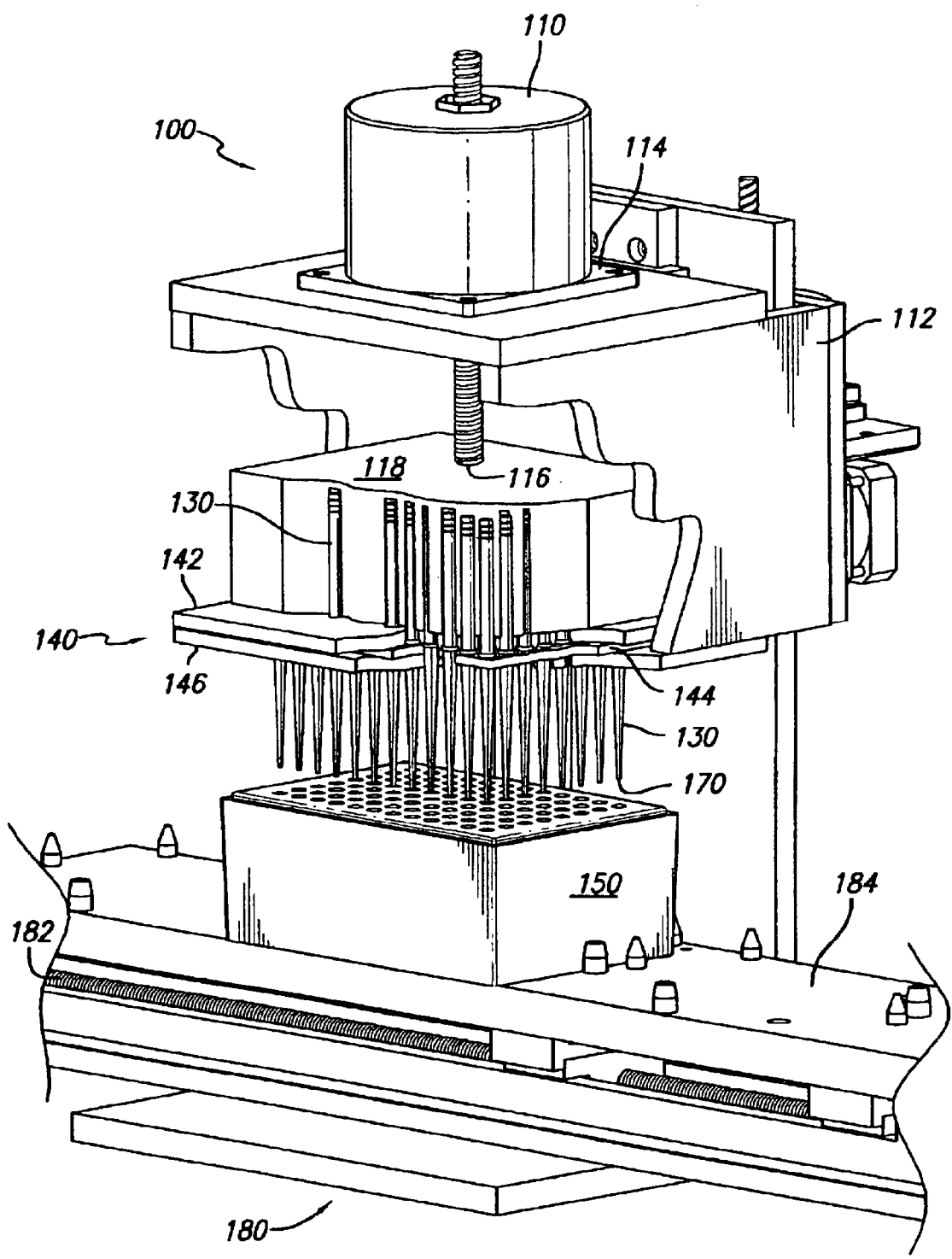
FIG. 5 is a left side and partial cutaway view of the pipettor of the present invention, including the pipette tip holder and the locked pipette tips with the chassis shown at a near maximal withdrawal distance that allows the pipette tips to clear the pipette holder.

FIG. 5 shows the lifting of the chassis 112 by the vertical displacement motor 192 so that the pipettes 130 are brought free from the pipette tip holder 150. As shown in FIG. 5, the pipette block 118 may be pulled vertically away from the locking plate assembly 140. In doing so, fluid (generally in the form of air) travels into the pipette 130 via the pipette tip 170 and into the pipette 130. The available volume for the pipette 130 is generally that of the pipette tip itself 130, as well as whatever volume of the bore 120 is present above the open proximal end 132 of the pipette tip 130. By moving the pipette block 118 relative to the locking plate assembly 140, the effective volume of the pipette tips is increased and decreased. The change in volume is made by changing the volume of the pipette block bore 120 above the circumscribing rib seals 134 adjacent the open proximal end 132 of the pipettes 130. In this way, by moving the pipette block vertically with respect to the locking plate assembly, the open proximal ends 132 of the pipette tips 130 travel further out of or into the pipette block bores 120. Fluid then enters or escapes the open tapered pipette tip openings 170 in order to aspirate or expel such fluids.

Also shown in FIG. 5 is a mechanical conveyor system 180 on which the pipette tip holder 150 sits. The mechanical conveyor 180 may have a precision screw 182 or the like that may move a conveyor platform 184 relative to the pipettor 100. In this way, pipette tip holders, microtiter receptacles, and the like can be precisely positioned below the pipette tip openings 170 for titration or pipetting.

As both the pipettor 100 and the mechanical conveyor system 180 are automated, and as automation of the placement and displacement of pipetting receptacles on the conveyor platform 184 is known in the art, it can be seen that the pipettor 100 of the present invention provides a very automated, as well as reliable, accurate and precise, means by which pipetting and titration can take place in the laboratory, factory, or otherwise. Such automation may be achieved robotically or otherwise, generally in a computer-aided fashion.

Figure 6:
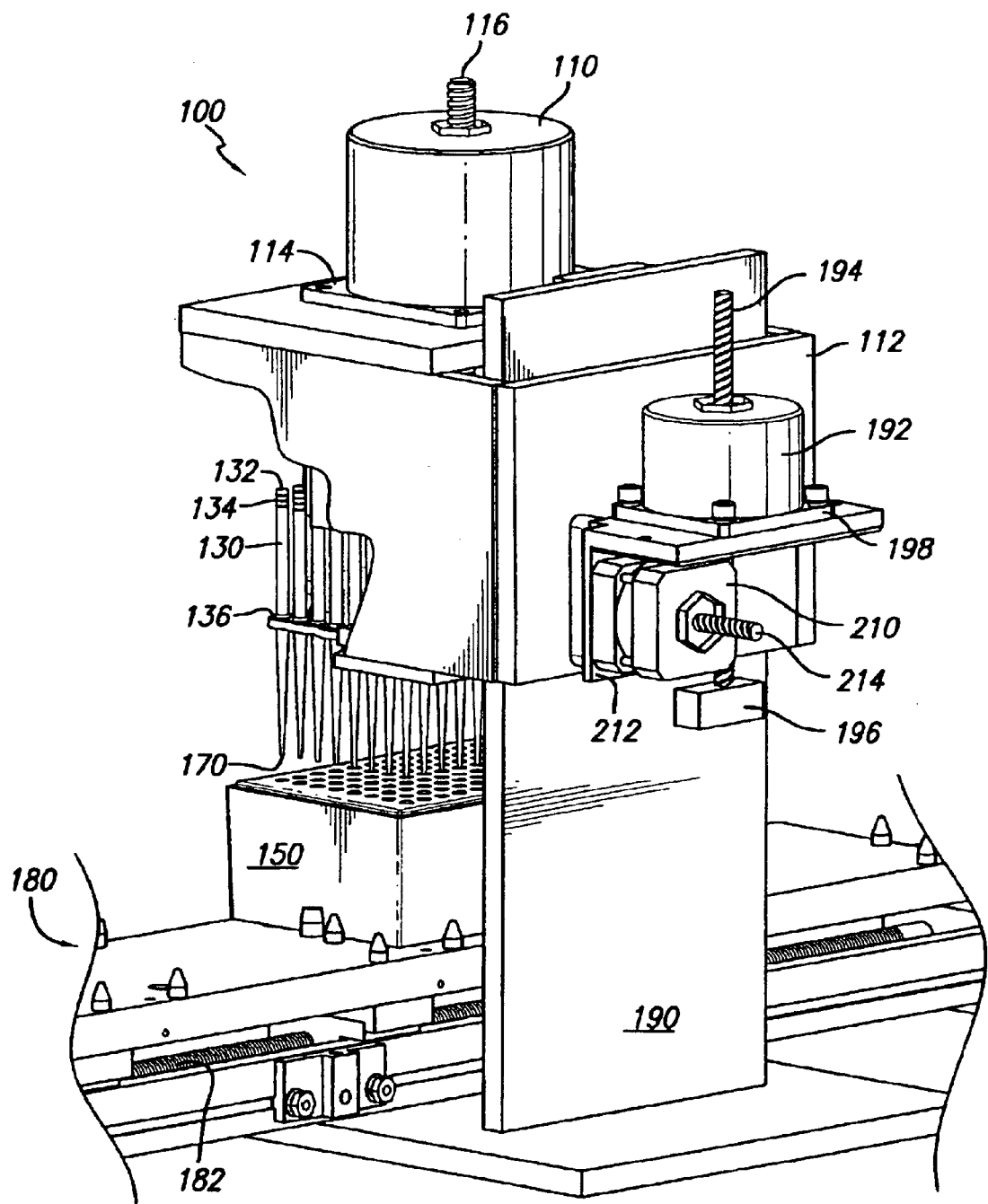
FIG. 6 is a left side rear and partial cutaway view of the pipettor of the present invention showing the locking plate motor and the vertical displacement motor structures.
Figure 7:
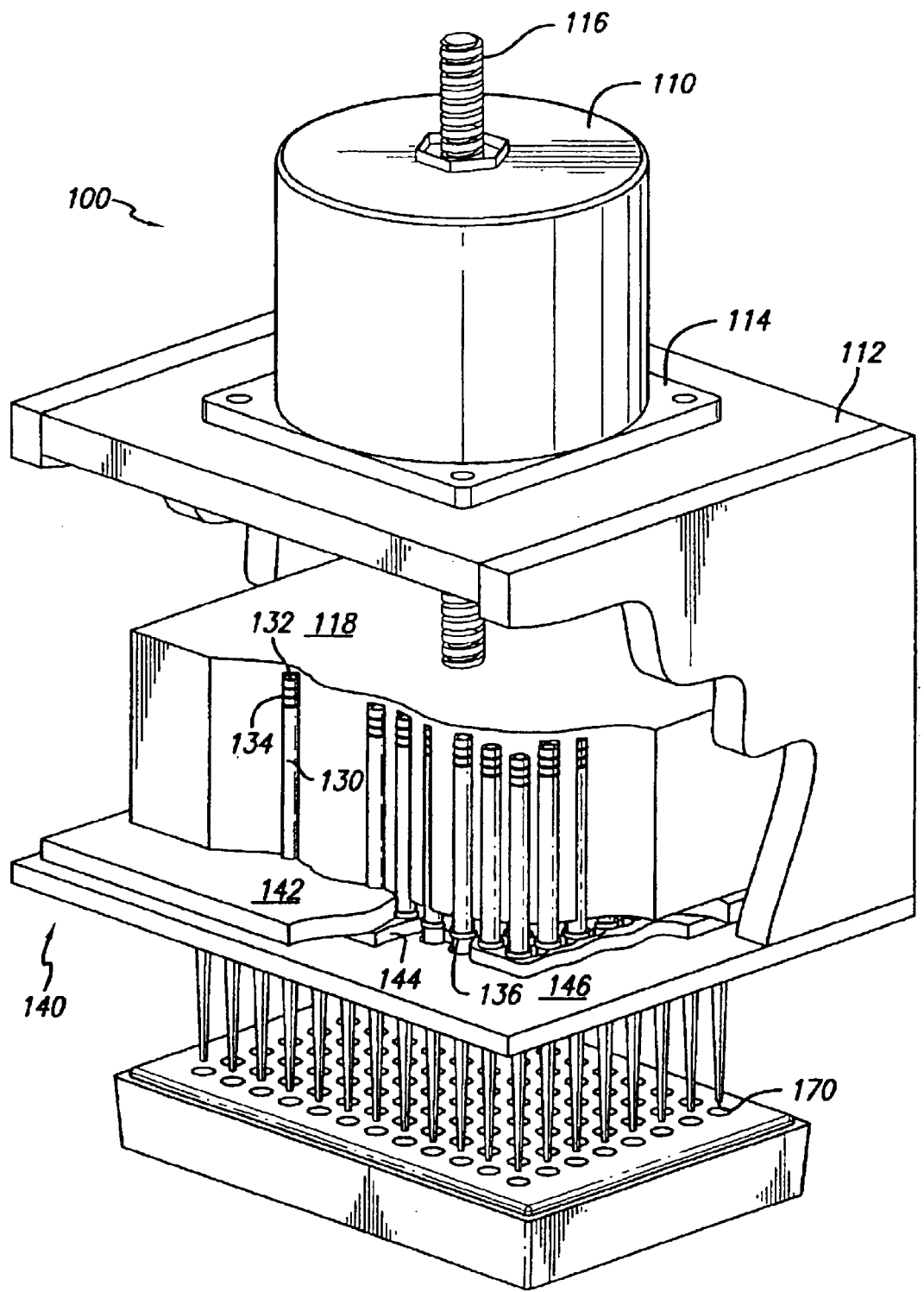
FIG. 7 is a left side perspective and partial cutaway view of the pipettor of the present invention, showing the pipette block in its fully dispensed position.
Figure 8:
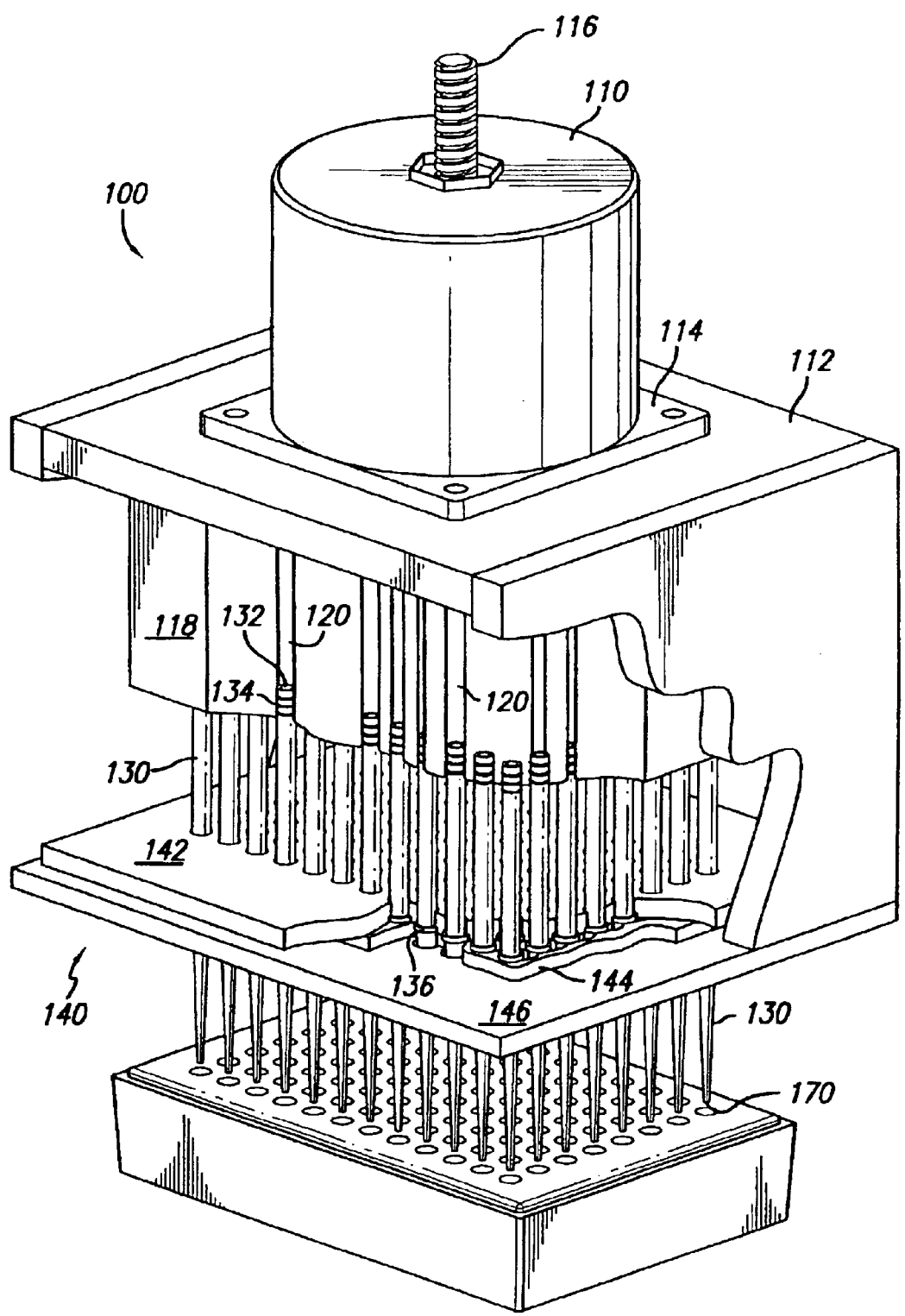
FIG. 8 is a left side perspective and partial cutaway view of the pipettor of the present invention with the pipette block at its maximal aspirated position.

FIG. 6 shows a rear perspective view of the pipettor 100, mechanical conveyor 180, as well as the vertical pipettor support 190. The mechanical pipettor support allows the chassis 112 to be disposed vertically with respect to the mechanical conveyor 180 by a vertical displacement motor 192. As shown in FIG. 6, a vertical displacement screw 194 rests upon a vertical displacement block stop 196 and passes through the vertical displacement motor 192. The vertical displacement motor may rotate an element in the manner of a threaded nut about the vertical displacement screw 194. As the vertical displacement screw 194 is rotationally fixed about its long axis with respect to the vertical displacement block stop 196, the vertical displacement screw does not turn with respect to the vertical pipettor support 190 or otherwise. Consequently, the turning of the internal member within the vertical displacement motor 192 causes the motor to travel along the length of the vertical displacement screw 194. Depending upon the direction that the motor 192 turns, the chassis 192 moves up or down with respect to the vertical pipettor support 190 as the vertical displacement motor 192 is fixed with respect to the chassis 112 as by a motor mount 198 or the like.

Also shown in FIG. 6 is the tip locking motor 210, which is mounted to the chassis via a locking motor mount 212 or the like. A locking plate screw 214 passes through the locking motor 210 and engages the locking plate 144. The locking plate 144 is then controlled by the motion of the locking plate screw as it travels relative to the locking motor 210. Depending upon the direction of travel of the locking motor 210, the locking plate screw 214 travels toward the chassis or away from the chassis respectively unlocking or locking the locking plate and any pipette tips 130 that are properly disposed with respect to the locking plate assembly 140.

Having described how the pipette tips 130 are engaged and operated by the pipettor 100 of the present invention, the process of pipette tip disengagement then occurs when the pipette block 118 disengages the open proximal pipette ends 132 by traveling sufficiently away from the locking plate assembly 140 so as to free itself from the pipette tips 130. As the locking plate assembly 140 holds the pipette tips 130 in place, the pipette block 118 may be lifted by the pipette block motor 110 so that it travels sufficiently high so as to disengage the open proximal ends 132 of the pipette tips 130. As there is no connection between the pipette tips 130 and the pipette block 118, the pipette block 118 can then free itself from the pipette tips.

Preferably, the chassis 112 has inserted the open tapered ends 170 of the pipette tips 130 into a pipette holder 150. Prior to the removal of the pipette block 118 from the pipettes 130. In so disposing the pipette tips 130, the removal of the pipette block 118 from the pipette tips 130 leaves the pipette tips 130 held in place only by the locking plate assembly 140. Upon disengagement of the pipette block 118, the locking plate assembly 140 may then disengage the tips 130 when the middle locking plate 144 travels forward. By gravity or otherwise, the pipette tips are then free to descend into the pipette tip holder 150 and the chassis 112 may be lifted away from the pipette tip holder 150, leaving the pipette tips 130 behind. Upon clearing the open proximal ends 132 of the pipette tips 130, the mechanical conveyor 180 may then dispose another set of pipette tips 130 in a pipette holder 150 beneath the pipettor 100 in order to repeat the engagement, pipetting, and disengagement processes. This cycle of engagement, pipetting, and disengagement may be repeated as many times as is desired.

Additionally, as means exist by which precise and accurate registration may be enabled between the pipettor 100 and pipette tip holders 150, this process may be highly automated. Such registration techniques can also be used for microtiter receptacles into which or from which fluids may be pipetted by the pipettor 100.

Figure 9:
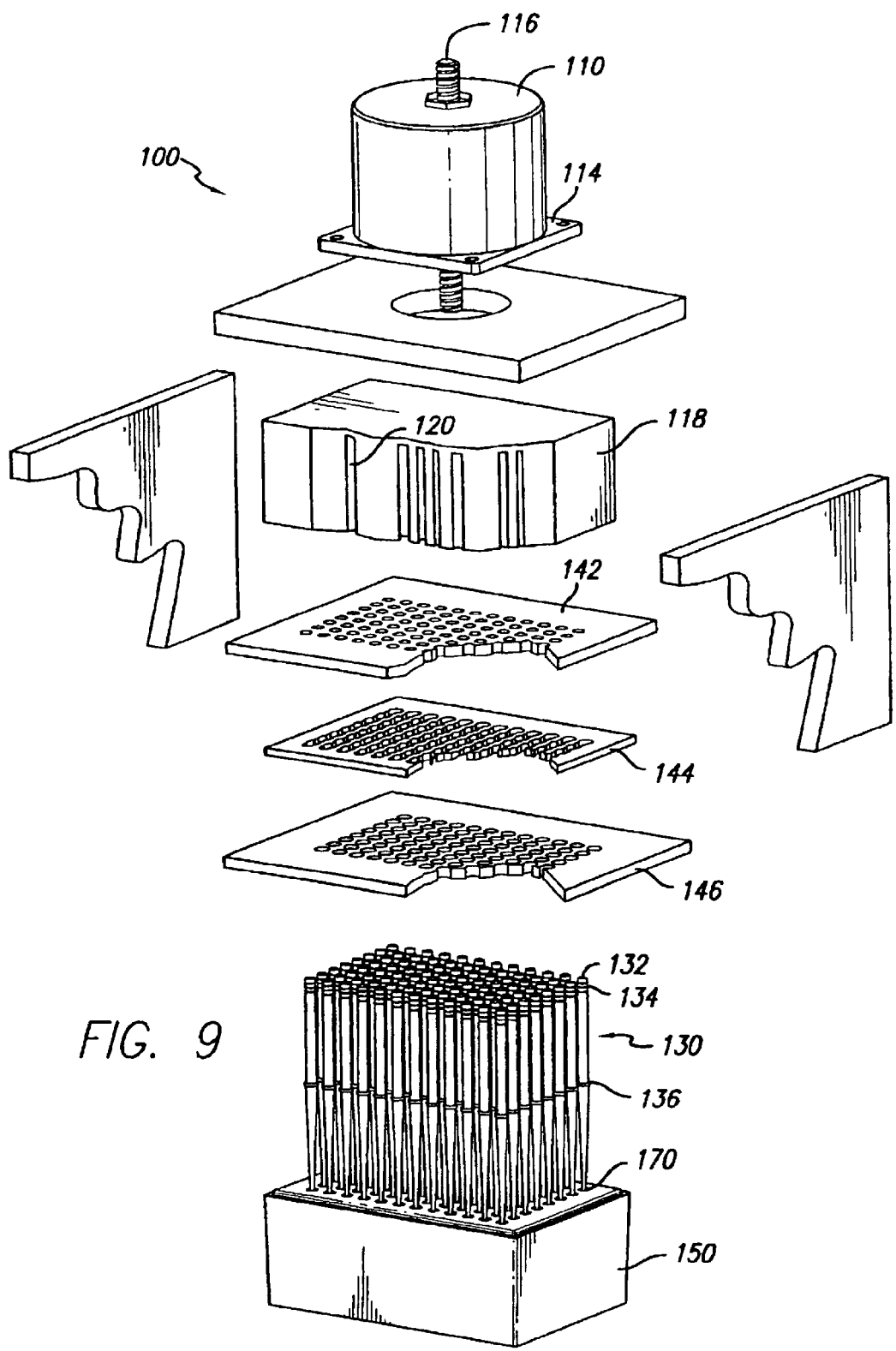
FIG. 9 is a left side perspective, partial cutaway, and exploded view of the pipettor system of the present invention with respect to the operating elements of the pipette block and the locking plate.

FIG. 9 shows an exploded view of the pipettor 100 with the vertical displacement and locking plate motors, as well as the vertical pipettor support are removed to better indicate the individual elements of the pipettor 100.

Figure 10:
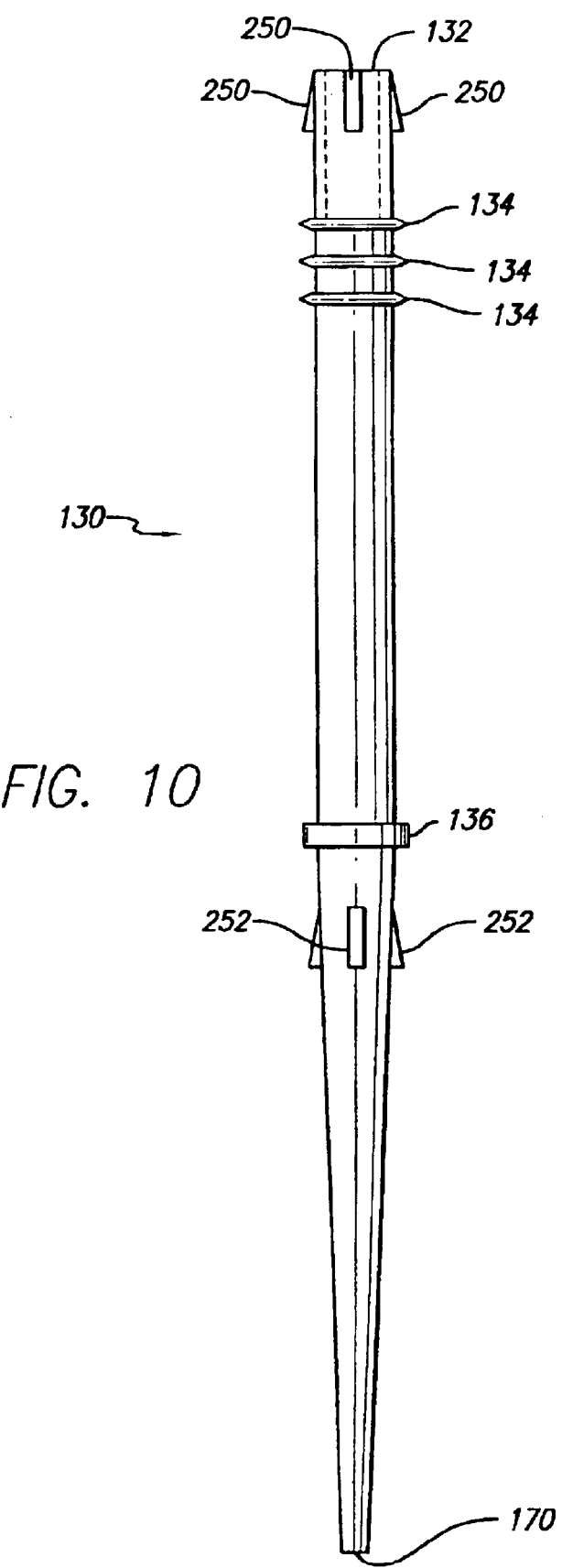
FIG. 10 is a side plan view of a pipette tip for use and conjunction with the pipettor of the present invention as well as other pipetting systems.

FIG. 10 shows an embodiment of a pipette tip 130 with a locking flange 136 and circumscribing sealing ribs 134. Additionally, at the open proximal end 132 of the pipette tip 130 are alignment taps or detents 250 which travel outwardly from the open proximal end 132 of the pipette tip 130. The alignment taps 250 serve as alignment means for the pipette tip 130 and angle outwardly to form a small right triangle with the pipette tip 130. The hypotenuse of this right triangle travels from a first end generally flush and adjacent to the open proximal end 132 and travels outwardly as the distance increases from the open proximal end 132. The height of the alignment tap at its terminal end is preferably less than or equal to the circumscribing and sealing ribs 134. This ensures that the ribs 134 act as a seal when they are compressed against the smooth sides of the pipette block bores 120.

The sealing ribs 134 may take several embodiments. As shown in FIG. 10, the sealing ribs are narrowly spaced apart and may form an accordion like structure with each rib having a pointed or edged perimeter. As the sealing ribs are generally made of the same material as the pipette tip 130 itself, the sealing ribs preferably provide a flexible perimeter that allows the establishment of a sliding seal with any circumscribing channel such as the holes 120 in the pipette block 118 (FIG. 1). The pointed nature of the sealing ribs 134 allows a significant degree of flexibility in such fins as well as giving the sealing ribs a high tolerance for different angles of engagement.

Alternative configurations from the pointed or finned perimeter of the sealing ribs 134 includes the use of rounded ribs, square ribs, oval perimeter ribs and the like.

The alignment taps 250 help to align the pipette tip 130 inside the bore 120 when the pipette block 118 engages the pipette tip 130 during the engagement process. If the axis of the pipette bore 120 is not parallel and/or aligned with that of the pipette tip 130, the alignment taps exert forces or torques upon the pipette tip 130 in order to better align it with the pipette block bore 120. This helps to ensure better engagement of the pipette tip 130 by the pipette block 118 and helps to ensure that such engagement is in an aligned manner so that the tapered, open, and operating end 170 of the pipette tips 130 are uniformly spaced with respect to one another as they are all centrally aligned and engaged with the pipette block bores 120. While FIG. 10 show three of four alignment taps 250 equally-spaced about the open proximal end 132 of the pipette tip 130, three equally-spaced taps 250 would also effectively balance the forces and torques to align the pipette tip 130 with any holder impressed onto the pipette tip end 132.

Figure 11:
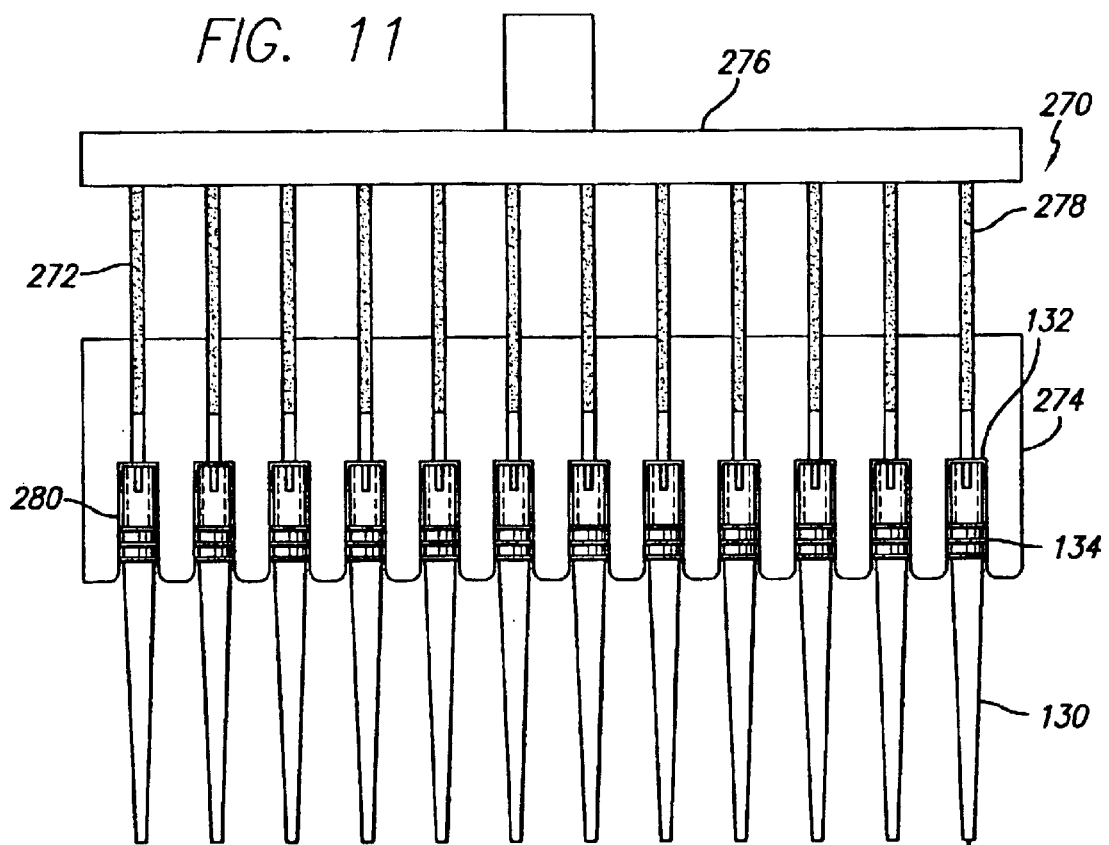
FIG. 11 is a side and partial cross sectional view of a series of pipette tips such as ones similar to that shown in FIG. 10 engaged in a piston-based pipette mandrel.
Figure 12:
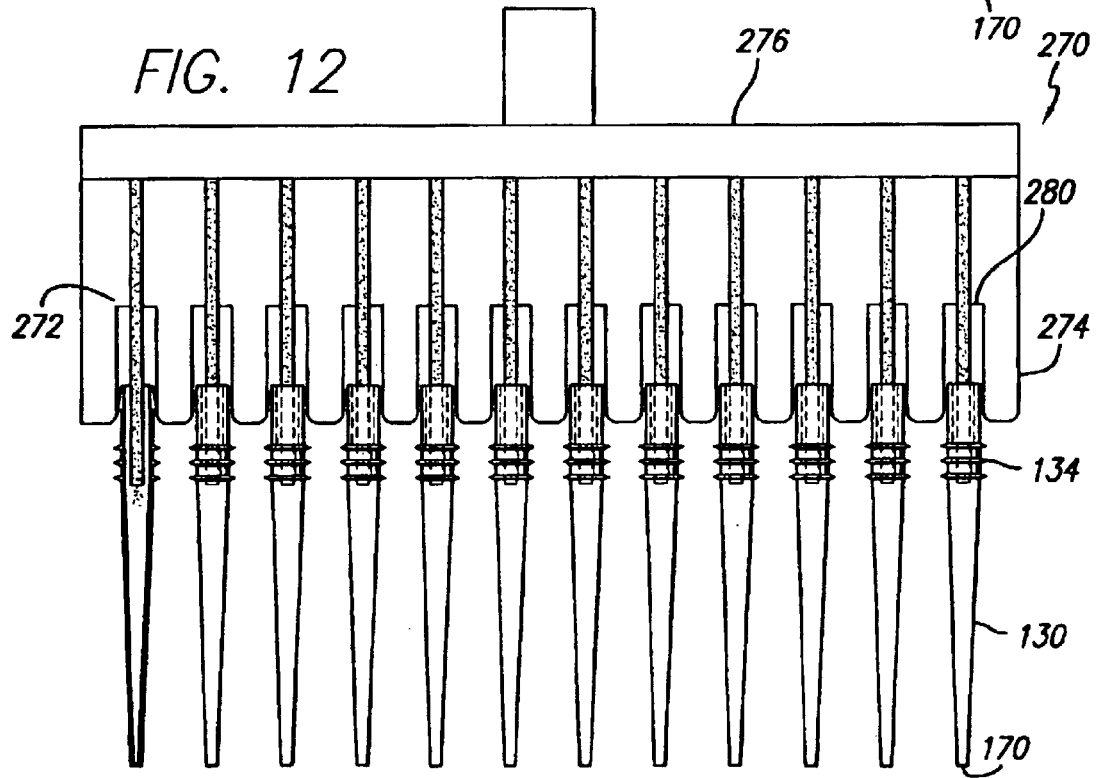
FIG. 12 is a side cross sectional view of the pipettor and pipette tips of FIG. 11 showing the ejection of the pipette tips by engagement with corresponding plungers.

As shown in FIGS. 11 and 12, the pipette tips 130 of the present invention may be used in conjunction with single row or other multiple row hand held or automatic pipettors 270. Such pipettors may be manual or automatic in nature and may use a series of plungers 272 in order to perform ejection of the tips and possibly additionally operate as the volume-changing element so as to perform pipetting operations through the pipette tip.

The pipettor 270 generally has a pipette block 274 into which the pipette tips 130 fit as described above. The process by which the pipette tips 130 fit into the pipette block 274 may be as described above with the pipette block 274 descending to engage the open proximal end 132 of the pipette tip as well as the sealing ribs 134. Once engaged by the pipette block 274, the pipette tips 130 may then be used for pipetting operations.

A slidable pipette plunger assembly 276 may engage the pipette block 274 through apertures or holes 278 present through the top of the pipette block 274. The plungers or pistons 272 are attached to the pipette plunger assembly 276 and by traveling into or out of the pipette block 274 to respectively expel or aspirate liquid volumes through the pipette tips 130.

When the pipette tips 130 are ready to be replaced, the pipette plunger assembly 276 descends into the pipette block 274. The plungers 272 then engage interior portions of the pipette tips 130 forcing them out of the pipette chambers 280. In this way, the pipette tips 130 are readily engaged by the pipette block 274 and are disengaged simultaneously by the plungers 272 of the pipette plunger assembly 276.

While the present invention has been described with regards to particular embodiments, it is recognized that additional variations of the present invention may be devised without departing from the inventive concept.

What is claimed is:

1. A pipette tip having an open proximal end and a tapered distal end comprising:

a first and second external and spaced-apart taps coupled to an exterior of the pipette tip adjacent the open proximal end, said first and second external taps adapted for engagement with a pipette tip holder; and a seal, said seal disposed below said first and second taps, said seal circumscribing the pipette tip and adapted to engage an interior of a pipette tip holder; whereby said first and second taps serve to align the pipette tip with a pipette tip holder when the pipette tip is externally about said open proximal end by said pipette tip holder and said seals the open proximal end of the pipette tip and inhibits fluid flow past said seal to urge said fluid flow only through the pipette tip and not past said seal.

2. A pipette tip having an open proximal end and a tapered distal end as set forth in claim 1, further comprising:

said first and second taps being oppositely opposed.

3. A pipette tip having an open proximal end and a tapered distal end as set forth in claim 1, further comprising:

a third external tap spaced apart from said first and second taps; and said first, second, and third taps equally spaced around the open proximal end; whereby forces and torques upon said first, second, and third taps are balanced so as to align the pipette tip with said pipette tip holder when said pipette tip holder engages the open proximal end and said first, second, and third taps.

4. A pipette tip having an open proximal end and a tapered distal end as set forth in claim 1, further comprising:

third and fourth external taps spaced apart from said first and second taps; and said first, second, third, and fourth taps equally spaced around the open proximal end; whereby forces and torques upon said first, second, third, and fourth taps are balanced so as to align the pipette tip with said pipette tip holder when said pipette tip holder engages the open proximal end and said first, second, third, and fourth taps.

5. A pipette tip having an open proximal end and a tapered distal end as set forth in claim 1, said seal further comprising:

a circumscribing rib.

6. A pipette tip having an open proximal end and a tapered distal end as set forth in claim 1, said seal further comprising:

three circumscribing ribs generally adjacent to one another.

7. A pipette tip having an open proximal end and a tapered distal end as set forth in claim 1, said seal further comprising:

said seal maintaining a sealing relationship with said pipette tip holder while said seal slides with respect to said pipette tip holder along said interior of said pipette tip holder.

8. A pipette tip having an open proximal end and a tapered distal end as set forth in claim 1, further comprising:

a locking flange coupled to the pipette tip.

9. A pipette tip having an open proximal end and a tapered distal end as set forth in claim 8, further comprising:

said locking flange circumscribing the pipette tip in a spaced-apart relationship from both the open proximal end and the tapered distal end.

10. A pipette tip having an open proximal end and a tapered distal end, comprising:

a seal proximate the open proximal end of the pipette tip and providing a seal about the open proximal end so that fluid does not flow past said seal;

said seal having a first sealing member, said first sealing member proximate the open proximal end of the pipette tip and providing a seal about the open proximal end so that fluid does not flow past said first sealing member;

second and third sealing members proximate said first sealing member, said second and third sealing members providing a seal about the open proximal end so that fluid does not flow past said second and third sealing members said first, second, and third sealing members each respectively having first, second, and third perimeters with first, second, and third edges; whereby said first, second, and third edges are flexible and flexibly engage an interior of a pipette tip holder to form said seal about the open proximal end of the pipette tip.

11. A pipette tip having an open proximal end and a tapered distal end as set forth in claim 10, wherein said first sealing member further comprises:

a first sealing rib circumscribing the pipette tip proximate the open proximal end.

12. A pipette tip having an open proximal end and a tapered distal end as set forth in claim 10, further comprising:

said second sealing member being a second sealing rib circumscribing the pipette tip proximate the open proximal end; and said third sealing member being a third sealing rib circumscribing the pipette tip proximate the open proximal end.

13. A pipette tip having an open proximal end and a tapered distal end as set forth in claim 10, said seal further comprising:

said seal maintaining a sealing relationship with said pipette tip holder while said seal slides with respect to said pipette tip holder along said interior of said pipette tip holder.

14. A pipette tip having an open proximal end and a tapered distal end as set forth in claim 10, further comprising:

alignment means for aligning the pipette tip with a pipette tip holder when the pipette tip is externally engaged about said open proximal end by said pipette tip holder.

15. A pipette tip having an open proximal end and a tapered distal end as set forth in claim 14, wherein said alignment means further comprises:

first and second external and spaced-apart taps coupled to an exterior of the pipette tip adjacent the open proximal end, said first and second external taps adapted for engagement with a pipette tip holder; whereby said first and second taps serve to align the pipette tip with a pipette tip holder when the pipette tip is externally engaged about said open proximal end by said pipette tip holder.

16. A pipette tip having an open proximal end and a tapered distal end as set forth in claim 15, further comprising:

said first and second taps being oppositely opposed.

17. A pipette tip having an open proximal end and a tapered distal end as set forth in claim 15, further comprising:

a third external tap spaced apart from said first and second taps; and said first, second, and third taps equally spaced around the open proximal end; whereby forces and torques upon said first, second, and third taps are balanced so as to align the pipette tip with said pipette tip holder when said pipette tip holder engages the open proximal end and said first, second, and third taps.

18. A pipette tip having an open proximal end and a tapered distal end as set forth in claim 15, further comprising:

third and fourth external taps spaced apart from said first and second taps; and said first, second, third, and fourth taps equally spaced around the open proximal end; whereby forces and torques upon said first, second, third, and fourth taps are balanced so as to align the pipette tip with said pipette tip holder when said pipette tip holder engages the open proximal end and said first, second, third, and fourth taps.

19. A pipette tip having an open proximal end and a tapered distal end as set forth in claim 15, further comprising:

said seal disposed below said first and second taps, said seal circumscribing the pipette tip and adapted to engage an interior of said pipette tip holder; whereby said seal seals the open proximal end of the pipette tip and inhibits fluid flow past said seal to urge said fluid flow only through the pipette tip and not past said seal.

20. A pipette tip having an open proximal end and a tapered distal end as set forth in claim 10, further comprising:

a locking flange coupled to the pipette tip.

21. A pipette tip having an open proximal end and a tapered distal end as set forth in claim 20, further comprising:

said locking flange circumscribing the pipette tip in a spaced-apart relationship from both the open proximal end and the tapered distal end.

22. A pipette tip having an open proximal end and a tapered distal end, comprising:

first and second external and spaced-apart taps coupled to an exterior of the pipette tip adjacent the open proximal end, said first and second external taps adapted for engagement with a pipette tip holder such that said first and second taps serve to align the pipette tip with a pipette tip holder when the pipette tip is externally engaged about said open proximal end by said pipette tip holder;

a seal, said seal disposed below said first and second taps, said seal circumscribing the pipette tip and adapted to engage an interior of said pipette tip holder such that said seal seals the open proximal end of the pipette tip and inhibits fluid flow past said seal to urge said fluid flow only through the pipette tip and not past said seal; and a locking flange coupled to the pipette tip, said locking flange circumscribing the pipette tip in a spaced-apart relationship from both the open proximal end and the tapered distal end.

23. A pipette tip having an open proximal end and a tapered distal end as set forth in claim 22, further comprising:

said first and second taps being oppositely opposed.

24. A pipette tip having an open proximal end and a tapered distal end as set forth in claim 22, further comprising:

a third external tap spaced apart from said first and second taps; and said first, second, and third taps equally spaced around the open proximal end; whereby forces and torques upon said first, second, and third taps are balanced so as to align the pipette tip with said pipette tip holder when said pipette tip holder engages the open proximal end and said first, second, and third taps.

25. A pipette tip having an open proximal end and a tapered distal end as set forth in claim 22, further comprising:
   third and fourth external taps spaced apart from said first and second taps; and
   said first, second, third, and fourth taps equally spaced around the open proximal end; whereby
   forces and torques upon said first, second, third, and fourth taps are balanced so as to align the pipette tip with said pipette tip holder when said pipette tip holder engages the open proximal end and said first, second, third, and fourth taps.

26. A pipette tip having an open proximal end and a tapered distal end as set forth in claim 22, said seal further comprising:
   a circumscribing rib.

27. A pipette tip having an open proximal end and a tapered distal end as set forth in claim 22, said seal further comprising:
   three circumscribing ribs generally adjacent to one another.

28. A pipette tip having an open proximal end and a tapered distal end as set forth in claim 22, said seal further comprising:
   said seal maintaining a sealing relationship with said pipette tip holder while said seal slides with respect to said pipette tip holder along said interior of said pipette tip holder.

29. A pipette tip having an open proximal end and a tapered distal end, comprising:
   first and second external and spaced-apart taps coupled to an exterior of the pipette tip adjacent the open proximal end, said first and second external taps aligning the pipette tip with a pipette tip holder and adapted for engagement with a pipette tip holder;
   a seal proximate the open proximal end of the pipette tip and providing a seal about the open proximal end so that fluid does not flow past said seal;
   said seal disposed below said first and second taps, said seal circumscribing the pipette tip and adapted to engage an interior of a pipette tip holder; whereby
   said seal seals the open proximal end of the pipette tip and inhibits fluid flow past said seal to urge said fluid only through the pipette tip and not past said seal.

\* \* \* \* \*